US005736152A

United States Patent [19]
Dunn

[11] Patent Number: 5,736,152
[45] Date of Patent: Apr. 7, 1998

[54] NON-POLYMERIC SUSTAINED RELEASE DELIVERY SYSTEM

[75] Inventor: Richard L. Dunn, Fort Collins, Colo.

[73] Assignee: Atrix Laboratories, Inc., Fort Collins, Colo.

[21] Appl. No.: 549,414

[22] Filed: Oct. 27, 1995

[51] Int. Cl.$^6$ .............................. A61F 2/02; A61K 47/30
[52] U.S. Cl. ........................................ 424/426; 514/772.3
[58] Field of Search ......................... 424/426; 514/772.3

[56] References Cited

U.S. PATENT DOCUMENTS

| | | | |
|---|---|---|---|
| 3,887,699 | 6/1975 | Yolles | 424/19 |
| 4,093,709 | 6/1978 | Chio et al. | 424/19 |
| 4,138,344 | 2/1979 | Chio et al. | 242/1 |
| 4,148,871 | 4/1979 | Pitt et al. | 424/19 |
| 4,292,965 | 10/1981 | Nash | 128/260 |
| 4,341,728 | 7/1982 | Robertson | 264/161 |
| 4,452,775 | 6/1984 | Kent | 424/19 |
| 4,675,189 | 6/1987 | Kent | 424/490 |
| 4,702,917 | 10/1987 | Schindler | 424/422 |
| 4,906,474 | 3/1990 | Langer et al. | 424/428 |
| 4,906,476 | 3/1990 | Radhakrishnan | 424/450 |
| 4,938,763 | 7/1990 | Dunn et al. | 604/891.1 |
| 5,077,049 | 12/1991 | Dunn et al. | 424/426 |
| 5,278,201 | 1/1994 | Dunn et al. | 523/113 |
| 5,278,202 | 1/1994 | Dunn et al. | 523/113 |
| 5,324,519 | 6/1994 | Dunn et al. | 424/426 |
| 5,324,520 | 6/1994 | Dunn et al. | 424/435 |
| 5,340,849 | 8/1994 | Dunn et al. | 523/113 |
| 5,368,859 | 11/1994 | Dunn et al. | 424/426 |
| B1 4,938,763 | 7/1995 | Dunn et al. | 604/891.1 |

FOREIGN PATENT DOCUMENTS

| | | |
|---|---|---|
| 0537559 (A1) | 4/1993 | European Pat. Off. . |
| 0539751 (A1) | 5/1993 | European Pat. Off. . |
| 0560014 (A1) | 9/1993 | European Pat. Off. . |
| 0649662 (A1) | 4/1995 | European Pat. Off. . |
| WO 88/07816 | 10/1988 | WIPO . |
| WO 9003768 (A1) | 4/1990 | WIPO . |
| WO 9101126 (A1) | 2/1991 | WIPO . |
| WO 9200718 (A1) | 1/1992 | WIPO . |
| WO 95/27481 | 10/1995 | WIPO . |

OTHER PUBLICATIONS

J. Folkman et al., *J. Surg. Res.* 4:139–142 (1964).
J. Posti, *Sci. Technol. Pract. Pharm.* 3(4):309–312 (1987).
Hsieh et al., *Drug Develop. & Ind. Pharm.* 13:2651–2666 (1987).
Shimkin et al., *Endocrinology* 29:1020 (1941).
Misra, *Research Monograph 28*, Willette et al., (eds.), National Institute on Drug Abuse (1981) pp. 253–264.

*Primary Examiner*—Carlos Azpuru
*Attorney, Agent, or Firm*—Merchant, Gould, Smith, Edell, Welter and Schmidt

[57] ABSTRACT

The invention relates to a method and composition for forming an implant in-situ within a body using non-polymeric materials, and the use of such implants as medical devices and drug delivery systems. The composition can be applied to an animal to treat periodontal disease or other tissue defect, enhance compatibility and performance of an implantable article, and deliver a biologically active agent.

20 Claims, No Drawings

NON-POLYMERIC SUSTAINED RELEASE DELIVERY SYSTEM

BACKGROUND OF THE INVENTION

Polymeric materials have been used for many years for producing medical devices such as sutures, surgical clips, catheters, vascular grafts, and implants. Such materials have also been used for the controlled release of biologically active agents with the discovery over 30 years ago that silicone elastomers could control the rate of release of lipophilic dyes (J. Folkman et al., *J. Surg. Res.* 4:139–142 (1964)). This led to the evaluation of silicone elastomers for the controlled release of pharmaceutical compounds. A number of these products have been commercialized, including the Norplant® subdermal implants for controlled release of levonorgestrel (J. Posti, *Sci. Technol. Pract. Pharm.* 32(4):309–312 (1987); see also, U.S. Pat. No. 4,341,728 (Robertson) and U.S. Pat. No. 4,292,965 (Nash, The Population Council, Inc.), and Compudose® implants (Eli Lilly and Company) for delivery of estradiol to promote growth in steers (Hsieh et al., *Drug Develop. & Ind. Pharm.* 13:2651–2666 (1987)). Other nonbiodegradable polymers such as polyethylene, poly(hydroxyethyl methacrylate) and ethylene-vinyl acetate copolymers have also been used for drug delivery.

More recently, biodegradable polymers have been used in drug delivery devices because of their biodegradability. These polymers include those based upon lactide, glycolide, ε-caprolactone and copolymers thereof (Yolles, U.S. Pat. No. 3,887,699; Kent, U.S. Pat. No. 4,675,189; Pitt, U.S. Pat. No. 4,148,871; Schindler, U.S. Pat. No. 4,702,917). Polyorthoesters and polyanhydrides have also been used as bioerodible matrices for drug release and as medical devices (U.S. Pat. Nos. 4,093,709 and 4,138,344, Choi and Heller; U.S. Pat. No. 4,906,474, Domb and Langer, M.I.T.).

The above-described polymers are solids at room temperature and, as a result, are shaped into solid structures outside the body and then inserted into the body by surgical procedures. If prepared as microparticles, microspheres, microcapsules or nanoparticles, such forms can be injected into the body using standard syringes and needles.

U.S. Pat. No. 4,938,763 (Dunn) describes methods and compositions in which biodegradable polymers are combined with biocompatible solvents to form a composition that can be administered into the body, whereupon the solvent diffuses or leaches away from the polymer composition into body fluids. Because the polymers are insoluble in water, they coagulate or precipitate upon contact with aqueous body fluid to form a solid implant for use as a medical device. If a drug is included in the polymer composition, it becomes incorporated into the implant matrix as the polymer coagulates.

A disadvantage of such a system is that a high concentration of organic solvent may be needed to fully dissolve the polymer. Polymeric compositions can also have a high flow viscosity because of the resistance of the long polymer chains to movement. In addition, the time period of biodegradation of some polymers can only by reduced to a certain minimum because of the need to hydrolyze the polymer chains to short chain lengths before the polymer becomes solubilized or metabolized. Therefore, there is a need for materials that are biodegradable, and will dissolve in biocompatible solvents to form a relatively non-viscous composition, and precipitate or coagulate to form a solid implant upon exposure to water.

Non-polymeric materials have been described for use as solid drug delivery matrices. Examples include cholesterol in the form of pellets for dispensing steroids (Shimkin et al., *Endocrinology* 29:1020 (1941)), naltrexone (Misra, "Narcotic antagonists: Naltrexone pharmochemistry and sustained release preparations," *Research Monograph* 28, Willette et al., eds., National Institute on Drug Abuse (1981), and a luteinizing hormone-releasing system (Kent, U.S. Pat. 4,452,775). Phospholipids are another non-polymeric material that have been used for preparing liposomes for drug delivery.

A disadvantage of those systems is that solid cholesterol pellets require a surgical incision or a large trochar for implantation. Although, the liposomes formed from phospholipids and from cholesterol can be injected using standard syringes and needles, these materials require considerable preparation, have low stability, and only a small amount of drug can be encapsulated within the small particles and released with time. In addition, because liposomes are small particles, they are poorly retained at the implantation site. Also, the small liposome particles are difficult to remove if complications arise and it is necessary to terminate treatment.

Accordingly, an object of the invention is to provide a composition made of non-polymeric material that can be used to provide a solid implant in-situ. Another object is to provide a solid implant that will provide a shorter biodegradation time than an implant formed from a biodegradable polymer. Yet another object is to provide a composition having a low flow viscosity that can be administered by a pressure applicator, and will form a solid biodegradable implant in-situ in a body for use as a medical device and/or a controlled delivery system for a drug.

SUMMARY OF THE INVENTION

The invention is directed to a non-polymeric composition for in situ formation of a solid matrix in an animal, and use of the composition as a medical device or as a sustained release delivery system for a biologically-active agent, among other uses.

The composition is composed of a biocompatible, non-polymeric material and a pharmaceutically-acceptable, organic solvent. The non-polymeric composition is biodegradable and/or bioerodible, and substantially insoluble in aqueous or body fluids. The organic solvent solubilizes the non-polymeric material, and has a solubility in water or other aqueous media ranging from miscible to dispersible. When placed into an implant site in an animal, the non-polymeric composition eventually transforms into a solid structure. The implant can be used for treating a tissue defect by enhancing cell growth and tissue regeneration, wound and organ repair, nerve regeneration, soft and hard tissue regeneration, and the like.

The composition can include a biologically-active agent (bioactive agent), as for example, an anti-inflammatory agent, an antiviral agent, antibacterial or antifungal agent useful for treating and preventing infections in the implant site, a growth factor, a hormone, and the like. The resulting implant provides a system for delivering the biologically-active agent to the animal.

The composition can also include optional ingredients such as a separate pore-forming agent for generating pores within the matrix, and/or a release rate modification agent for controlling the rate of breakdown of the implant matrix and/or the rate of release of a bioactive agent in vivo from the implant matrix. Examples of pore-forming agents include sucrose, sodium chloride, sodium carbonate, a cellulose-based polymer, and the like. Examples of release rate modification agents include dimethyl citrate, triethyl citrate, ethyl heptanoate, glycerin, hexanediol, and the like. The composition can also include a controlled release component associated with the active agent to control its release from the composition during formation of the implant and/or from the formed implant. Examples of controlled release components include a microcapsule, microsphere, liposome, nanoparticle or other microstructure; a fiber, bead or other macrostructure; a low water-solubility salt of the agent; a complex or covalently-bonded conjugate of the agent and. a carrier molecule; and the like.

To form a solid implant in situ, the composition can be placed in a syringe and injected into the body of an animal using a standard needle. The injection may be subcutaneous, intramuscular, intraperitoneal, intralesional, and the like. The composition can also be dispensed by brushing or squirting it onto the surface of a tissue. The material can also be administered as a spray from an aerosol dispensing device under pressure, from a pump dispenser, or other pressure applicator.

The composition can be applied to an implant site such as a void, a tissue defect, surgical incision, the surface of the skin to cover a burn area or surface wound, and the like. The composition is flowable with a consistency that ranges from watery to slightly viscous to a putty or paste. The non-polymeric material will eventually coagulate to a microporous, solid matrix upon the dissipation of the organic solvent into adjacent tissue fluids. Unlike a solid implant, the non-polymeric composition can be manipulated and shaped within the defect site as it solidifies. Advantageously, the moldability of the composition as it hardens allows it to conform to irregularities, crevices, cracks, holes, and the like, in the implant site. The resulting solid matrix is biodegradable, bioabsorbable, and/or bioerodible, and will be gradually absorbed into the surrounding tissue fluids, and become disintegrated through enzymatic, chemical and/or cellular hydrolyric action.

Advantageously, the present non-polymeric composition has a lower flow viscosity than polymeric compositions. Because of this property, compositions can be formulated with a high solid content and low amount of solvent to provide a fluid form that can be administered using a pressure applicator such as injection into tissue through a syringe and needle. The non-polymeric materials can also be used where a high rate of degradation is desired because they are single molecules and require only one hydrolysis reaction before becoming solubilized and metabolized by the body. The non-polymeric compositions can also be enzymatically degraded by mechanisms other than hydrolysis. As such, matrices formed from these materials are degraded from the surface resulting in a bioerodible implant.

DETAILED DESCRIPTION OF THE INVENTION

The invention provides a biodegradable composition composed of a biodegradable, water-coagulable, non-polymeric material and a biocompatible, non-toxic organic solvent that is miscible to dispersible in an aqueous medium. Upon implantation in the body of an animal, the organic solvent will dissipate, disperse or leach from the composition into surrounding tissue fluid, and the non-polymeric material will gradually coagulate or precipitate to form a solid, microporous matrix. The resulting implant has a variety of uses, as for example, as a barrier system for enhancing cell growth and tissue regeneration, delivery of a biologically-active agent such as a drug or medicament, among other applications. The composition and resulting solid implant are biocompatible in that neither the non-polymeric material, the solvent nor the solid matrix cause substantial tissue irritation or necrosis at the implant site.

As used herein, the term "implant site" is meant to include a site, in or on which the non-polymeric composition is applied, as for example, a soft tissue such as muscle or fat, or a hard tissue such as bone. Examples of implant sites include a tissue defect such as a tissue regeneration site; a void space such as a periodontal pocket, surgical incision or other formed pocket or cavity; a natural cavity such as the oral, vaginal, rectal or nasal cavities, the cul-de-sac of the eye, and the like; and other sites into or onto which the composition may be placed and formed into a solid implant including a skin surface defect such as a cut, scrape or burn area. The term "biodegradable" means that the non-polymeric material and/or matrix of the implant will degrade over time by the action of enzymes, by simple or enzymatically catalyzed hydrolyric action and/or by other similar mechanisms in the human body. By "bioerodible," it is meant that the implant matrix will erode or degrade over time due, at least in part, to contact with substances found in the surrounding tissue fluids, cellular action, and the like. By "bioabsorbable," it is meant that the non-polymeric matrix will be broken down and absorbed within the human body, for example, by a cell, a tissue, and the like.

Non-Polymeric Material.

Non-polymeric materials useful in the present compositions are those that are biocompatible, substantially insoluble in water and body fluids, and biodegradable and/or bioerodible within the body of an animal. The non-polymeric material is capable of being at least partially solubilized in a water-soluble organic solvent. The non-polymeric materials are also capable of coagulating or solidifying to form a solid implant matrix upon the dissipation, dispersement or leaching of the solvent component from the composition and contact of the non-polymeric material with an aqueous medium. The solid matrix has a firm consistency ranging from gelatinous to impressionable and moldable, to a hard, dense solid.

Non-polymeric materials that can be used in the composition generally include any having the foregoing characteristics. Examples of useful non-polymeric materials include sterols such as cholesterol, stigmasterol, β-sitosterol, and estradiol; cholestery esters such as cholesteryl stearate; $C_{12}$–$C_{24}$ fatty acids such as lauric acid, myristic acid, palmitic acid, stearic acid, arachidic acid, behenic acid, and lignoceric acid; $C_{18}$–$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$–$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lyso-derivatives thereof; sphingosine and derivatives thereof;

spingomyelins such as stearyl, palmitoyl, and tricosanyl spingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glycerol tristearate, stearic acid, stearic anhydride, glyceryl monocleate, glyceryl monolinoleate, and acetylated monoglycerides.

The non-polymeric material is combined with a compatible and suitable organic solvent to form a composition that has the desired consistency ranging from watery to viscous to a spreadable putty or paste. The consistency of the composition will vary according to factors such as the solubility of the non-polymeric material in the solvent, the concentration of the non-polymeric material in the formulation, the concentration of the biologically active agent in the formulation, and/or the presence of additives. The solubility of a non-polymeric material in a particular solvent will vary according to factors such as its crystallinity, hydrophilicity, ionic character and lipophilicity. Accordingly, the ionic character and the concentration of the non-polymeric material in the solvent can be adjusted to achieve the desired solubility. Highly preferred non-polymeric materials are those that have low crystallinity, nonpolar characteristics, and are more hydrophobic.

Organic Solvents.

Suitable organic solvents are those that are biocompatible, pharmaceutically-acceptable, and will at least partially dissolve the non-polymeric material. The organic solvent has a solubility in water ranging from miscible to dispersible. The solvent is capable of diffusing, dispersing, or leaching from the composition in situ into aqueous tissue fluid of the implant site such as blood serum, lymph, cerebral spinal fluid (CSF), saliva, and the like. Preferably, the solvent has a Hildebrand (HLB) solubility ratio of from about 9–13 (cal/cm$^3$)$^{1/2}$. It is preferred that the degree of polarity of the solvent is effective to provide at least about 5% solubility in water.

Solvents that are useful include, for example, substituted heterocyclic compounds such as N-methyl-2-pyrrolidone (NMP) and 2-pyrrolidone (2-pyrol); esters of carbonic acid and alkyl alcohols such as propylene carbonate, ethylene carbonate and dimethyl carbonate; fatty acids such as acetic acid, lactic acid and heptanoic acid; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; ether alcohols such as 2-ethoxyethanol, ethylene glycol dimethyl ether, glycofurol and glycerol formal; alcohols such as ethanol and propanol; polyhydroxy alcohols such as propylene glycol, polyethylene glycol (PEG), glycerin (glycerol), 1,3-butyleneglycol, and isopropylidene glycol (2,2-dimethyl-1,3-dioxolone-4-methanol; Solketal); dialkylamides such as dimethylformamide, dimethylacetamide; dimethylsulfoxide (DMSO) and dimethylsulfone; tetrahydrofuran; lactones such as ε-caprolactone and butyrolactone; cyclic alkyl amides such as caprolactam; aromatic amides such as N,N-dimethyl-m-toluamide, and 1-dodecylazacycloheptan-2-one; and the like; and mixtures and combinations thereof. Preferred solvents include N-methyl-2-pyrrolidone, 2-pyrrolidone, dimethylsulfoxide, ethyl lactate, propylene carbonate, glycofurol, glycerol formal, and isopropylidene glycol.

A mixture of solvents providing varying degrees of solubility for the non-polymeric material can be used to increase the coagulation rate of the non-polymeric materials that exhibit a slow coagulation or precipitation rate in an aqueous medium. For example, the non-polymeric material can be combined with a mixture of a good solvent (i.e., solvent that can solubilize the non-polymeric material to a high degree) and a poorer solvent (i.e., solvent that can solubilize the non-polymeric material to a low degree) or a non-solvent (i.e., solvent in which the non-polymeric material is substantially insoluble). It is preferred that a coagulant-promoting solvent system is composed of an effective amount of a good solvent and a poorer or non-solvent such that the non-polymeric material will remain solubilized in the composition until applied to a tissue, and then coagulate or precipitate upon dissipation or diffusion of solvent from the composition into adjacent tissue fluids.

The concentration of the non-polymeric material in the composition will generally accomplish rapid and effective dissipation of the solvent and coagulation of the non-polymer material when administered to an implant site. This concentration can range from about 0.01 gram of the non-polymer material per ml of solvent, to about 19 grams per ml of solvent, preferably from about 0.1 gram to about 6 grams per ml.

Upon contact with an aqueous medium such as water or a body fluid, the solvent diffuses or leaches from the composition into the aqueous medium, and the non-polymeric material coagulates to form a solid matrix. Preferably, the non-polymeric material solidifies in situ to a solid matrix within about 1–5 days after implantation, preferably within about 1–3 days, preferably within about 2 hours.

Optionally, the composition of non-polymeric material can be combined with a minor amount of a biodegradable, bioabsorbable thermoplastic polymer such as a polylactide, polycaprolactone, polyglycolide, or copolymer thereof, to provide a more coherent solid implant or a composition with greater viscosity so as to hold it in place while it solidifies. Such thermoplastic polymers are disclosed in U.S. Pat. No. B1 4,938,763 to Dunn et al. (issued Jul. 3, 1990, certificate issued Jul. 4, 1995), the disclosure of which is incorporated by reference herein.

Pore Formation and Pore-Forming Agents.

The solid, non-polymeric matrix that is formed from the composition has a microporous structure. Pores are formed within the solid matrix of the implant by several means. The dissipation, dispersement or diffusion of the solvent out of the solidifying, coagulating, non-polymeric matrix into the adjacent tissue fluids may generate pores, including pore channels, in the matrix. The size of the pores of the solid implant are in the range of about 1–500 microns, and the solid matrix has a porosity in the range of about 5–95%.

The action of the solvent as it moves out of the coagulating non-polymeric composition results in a solid matrix that is a two-layer pore structure of a highly porous inner core portion and a comparatively less porous outer microporous skin. The pores of the inner core portion are preferably substantially uniform and the skin of the solid implant is relatively non-porous compared to the porous nature of the core. Preferably, the outer skin portion of the implant has pores with diameters significantly smaller in size than the pores in the inner core portion. Preferably, the size of pores of the skin layer is about 0,001 microns up to about 50 microns in diameter.

Optionally, a pore-forming agent can be included in the composition to generate additional pores in the implant matrix. The pore-forming agent can be any organic or inorganic, pharmaceutically-acceptable substance that is substantially soluble in water or body fluid, and will dissipate from the coagulating non-polymeric material and/or the solid matrix of the implant into surrounding body fluid at the implant site. The porous matrices formed through the inclusion of a pore-forming agent have a pore structure in which the pores are substantially similar in size throughout.

It is preferred that the pore-forming agent is insoluble in the organic solvent to form a uniform mixture with the non-polymeric material. The pore-forming agent may also be a water-immiscible substance that rapidly degrades to a water-soluble substance. Preferably, the pore-forming agent is combined with the non-polymeric material and organic solvent in admixture before the solid matrix is formed. Suitable pore-forming agents that can be used in the composition include, for example, sugars such as sucrose and dextrose, salts such as sodium chloride and sodium carbonate, polymers such as hydroxylpropylcellulose, carboxymethylcellulose, polyethylene glycol and polyvinylpyrrolidone, and the like. Solid crystals that will provide a defined pore size, such as salt or sugar, are preferred.

When the composition is administered to an implant site, the solvent and/or pore-forming agent disperses, dissipates or dissolves into surrounding tissue fluids. This causes the formation of microporous channels within the coagulating matrix. Optionally, the pore-forming agent may dissipate from the solid matrix into the surrounding tissue fluids at a rate slower than that of the solvent, or be released from the matrix over time by biodegradation or bioerosion of the matrix. Preferably, the pore-forming agent dissipates from the coagulating implant matrix within a short time following implantation such that a matrix is formed with a porosity and pore structure effective to perform the particular purpose of the implant, as for example, a barrier system for a tissue regeneration site, a matrix for timed-release of a drug or medicament, and the like.

Porosity of the solid implant matrix may be varied by the concentration of water-soluble or water-dispersible ingredients, such as the solvent and/or pore-forming agent, in the composition. For example, a high concentration of water-soluble substances in the composition may produce a matrix having a high degree of porosity. The concentration of the pore-forming agent relative to the non-polymeric material in the composition may be varied to achieve different degrees of pore-formation, or porosity, in the matrix. Generally, where included, the composition will include about 0.01–1 gram of pore-forming agent per gram of the non-polymeric material.

The size or diameter of the pores formed in the matrix of the solid implant can be modified according to the size and/or distribution of the pore-forming agent within the implant matrix. For example, pore-forming agents that are relatively insoluble in the non-polymeric mixture may be selectively included in the composition according to particle size in order to generate pores having a diameter that corresponds to the size of the pore-forming agent. Pore-forming agents that are soluble in the non-polymeric mixture may be used to vary the pore size and porosity of the implant matrix by the pattern of distribution and/or aggregation of the pore-forming agent within the mixture and the coagulating and solid matrix.

Where the implant is used to promote guided tissue regeneration, it is preferred that the diameter of the pores in the matrix are effective to deter growth of epithelial cells and enhance growth of connective tissue cells into the matrix of the implant. It is further preferred that the size of the pores and porosity of the matrix facilitate diffusion of nutrients and other growth-promoting substances such as growth factors, to cells which have grown into the matrix. Preferably, the degree of porosity of the matrix provides an implant that is capable of substantially maintaining structural integrity for the desired period of time without breakage or fracturing during use.

To provide an effective implant for bone cell regrowth and tissue regeneration, it is preferred that the diameter of the pores of the implant is about 3–500 microns, more preferably about 25–200 microns, more preferably about 75–150 microns. It is further preferred that the matrix has a porosity of about 5–95%, preferably about 25–85%, in order to provide optimum cell and tissue ingrowth into the matrix and optimum structural integrity.

Pore diameter and distribution within the solid non-polymeric matrix may be measured, for example, according to scanning electron microscopy methods by examination of cross-sections of the matrix. Porosity of the non-polymeric matrix may be measured according to suitable methods known in the art, as for example, mercury intrusion porosimetry, specific gravity or density comparisons, calculation from scanning electronic microscopy photographs, and the like. Additionally, porosity may be calculated according to the proportion or percent of water-soluble material included in the composition. For example, a composition that contains about 30% non-polymeric material and about 70% solvent and/or other water-soluble components will generate an implant having a polymer matrix of about 70% porosity.

Biologically-Active Agent.

Optionally, the composition can provide a system for sustained, continuous delivery of drugs, medicaments and other biologically-active agents to tissues adjacent to or distant from the implant site. The biologically-active agent is capable of providing a local or systemic biological, physiological or therapeutic effect in the body of an animal. For example, the agent may act to control infection or inflammation, enhance cell growth and tissue regeneration, control tumor growth, enhance bone growth, among other functions.

The biologically-active agent is preferably soluble or dispersible in the non-polymeric composition to form a homogeneous mixture, and upon implantation, becomes incorporated into the implant matrix. As the solid matrix degrades over time, the biologically-active agent is capable of being released from the matrix into the adjacent tissue fluid, and to the pertinent body tissue or organ, either adjacent to or distant from the implant site, preferably at a controlled rate. The release of the biologically-active agent from the matrix may be varied, for example, by the solubility of the biologically-active agent in an aqueous medium, the distribution of the agent within the matrix, the size, shape, porosity, and solubility and biodegradability of the solid matrix.

The non-polymeric composition and solid matrix include the biologically-active agent in an amount effective to provide the desired level of biological, physiological, pharmacological and/or therapeutic effect in the animal. The biologically-active agent may stimulate or inhibit a biological or physiological activity within the animal. There is generally no critical upper limit on the amount of the bioactive agent that can included in the composition. The only limitation is a physical limitation for advantageous application, for example, the concentration of the bioactive agent should not be so high that the composition has a consistency that inhibits its delivery to the implant site by the desired method. The lower limit of the amount of bioactive agent incorporated into the composition will depend on the activity of the bioactive material and the period of time desired for treatment. The bioactive agent is gradually released from the solid matrix in vivo by diffusion, dissolution and/or biodegradation of the non-polymeric material.

Examples of biologically-active agents that are useful include substances capable of preventing an infection systemically in the animal or locally at the defect site, as for example, anti-inflammatory agents such as hydrocortisone, prednisone, and the like; antibacterial agents such as penicillin, cephalosporins, bacitracin, tetracycline, doxycycline, gentamycin, quinolines, neomycin, clindamycin, kanamycin, metronidazole, and the like; antiparasitic agents such as quinacrine, chloroquine, vidarabine, and the like; antifungal agents such as nystatin, and the like; antiviral agents such as acyclovir, ribarivin, interferons, and the like; analgesic agents such as salicylic acid, acetaminophen, ibuprofen, naproxen, piroxicam, flurbiprofen, morphine, and the like; local anaesthetics such as cocaine, lidocaine, bupivacaine, benzocaine, and the like; immunogens (vaccines) for stimulating antibodies against hepatitis, influenza, measles, rubella, tetanus, polio, rabies, and the like; peptides such as leuprolide acetate (an LH-RH agonist), nafarelin, ganirelix, and the like.

Also useful is a substance or metabolic precursor thereof, which is capable of promoting growth and survival of cells and tissues or augmenting the functioning of cells, as for example, a nerve growth promoting substance such as a ganglioside, a nerve growth factor, and the like; a hard or soft tissue growth promoting agent such as fibronectin (FN), human growth hormone (HGH), a colony stimulating factor, bone morphogenetic protein, platelet-derived growth factor (PDGP), insulin-derived growth factor (IGF-I, IGF-II), transforming growth factor-alpha (TGP-α), transforming growth factor-β (TGP-β), epidermal growth factor (EGF), fibroblast growth factor (FGF), interleukin-1 (IL-1), and the like; an osteoinductive agent or bone growth promoting substance such as bone chips, demineralized freeze-dried bone material, and the like; and antineoplastic agents such as methotrexate, 5-fluorouracil, adriamycin, vinblastine, cisplatin, tumor-specific antibodies conjugated to toxins, tumor necrosis factor, and the like.

Other useful substances include hormones such as progesterone, testosterone, and follicle stimulating hormone (FSH) (birth control, fertility-enhancement), insulin, somatotropins, and the like; antihistamines such as diphenhydramine, chlorphencramine and the like; cardiovascular agents such as digitalis, nitroglycerine, papaverine, streptokinase and the like; anti-ulcer agents such as cimetidine hydrochloride, isopropamide iodide, and the like; bronchodilators such as metaproternal sulfate, aminophylline, and the like; vasodilators such as theophylline, niacin, minoxidil, and the like; central nervous system agents such as a tranquilizer, B-adrenergic blocking agent, dopamine, and the like; antipsychotic agents such as risperidone, olanzapine; narcotic antagonists such as naltrexone, naloxone, buprenorphine; and other like substances.

For further examples of biologically-active agents that may be used in the present invention, see U.S. Pat. No. 5,324,519, the disclosure of which is incorporated by reference herein.

Control of Matrix Breakdown.

The solid, non-polymeric matrix is capable of biodegradation, bioerosion and/or bioabsorption within the implant site of the animal. Generally, the implant matrix will breakdown over a period from about 2 weeks to about 12 months, preferably within about 2–12 weeks, preferably within about 14–60 days. The rate of breakdown of the implant can be controlled by varying the type, amount, and hydrophilicity of the non-polymeric material, by including a pore-forming agent, and/or by varying the concentrations of ingredients that comprise the non-polymeric composition.

For example, the amount and choice of non-polymeric material can vary the length of time the solid matrix is to be maintained within the implant site from a few days or weeks to several months. When the implant is used to enhance cell growth and tissue regeneration, it is preferred that the solid matrix will disintegrate at a rate effective to allow displacement of the matrix by cell growth from the adjacent cells or tissue, preferably about 2–8 weeks.

Modification of Release Rate of the Bioactive Agent.

A wide range of release rates of the biologically-active agent from the solidified matrix from relatively fast to relatively slow, or from slow to faster, can be achieved by a number of rate release controls. Such controls include adjusting the concentration of the non-polymeric material and bioactive agent in the composition, use of a release rate modification agent, and/or modifying the breakdown of the solid matrix, i.e., by varying the non-polymeric material that is used, by inclusion of a pore-forming agent, and the like.

The rate of release of the bioactive agent from the solid matrix can be adjusted by varying the concentration of ingredients in the composition. For example, a composition composed of a lower concentration of the non-polymeric material will form a matrix from which the bioactive agent will be more readily released.

A release rate modification agent can be included in the composition with the non-polymeric material and organic solvent to vary the rate of release of a biologically-agent from the solid matrix as desired, and provide controlled, sustained release of the bioactive agent. The release rate modification agent can be an organic substance that is water-miscible to water-dispersible, or water-insoluble. The release modification agent is compatible with the non-polymeric material and organic solvent of the composition, and preferably pharmaceutically-acceptable. Preferably, where a release rate modification agent is included, the composition contains about 0.5–15%, preferably about 5–10% of the agent.

The release rate modification agent can be a plasticizing compound such as epoxidized soybean oil, and other epoxidized vegetable oils. The release modifying agent can also be an organic solvent such as those described for solubilizing the non-polymeric material in the composition, but different from the primary organic solvent that is used. For example, the non-polymeric material and bioactive agent can be solubilized in N-methyl-2-pyrrolidone, and a minor but effective amount of another organic solvent such as dimethyl adipate can be added to the composition to modify the rate of release of the bioactive agent from the solidified matrix. Preferred organic solvent release modifying agents include propylene glycol, polyethylene glycol, ethyl heptanoate, dimethyl adipate, glyceryl triacetate, and dimethyl phthalate. A rate release modifying agent can be used singly or in combination. Suitable combinations of organic solvents as release modifying agents include, for example, glycerin/propylene glycol, sorbitol/glycerine, and the like.

The use of a release rate modification agent may either decrease or increase the release of the bioactive agent. For example, the inclusion of a hydrophobic compound such as ethyl heptanoate can slow the release of the bioactive agent from the solid matrix, while a hydrophilic substance such as polyethylene glycol may increase the release of the bioactive agent.

Controlled Release Component.

The composition can also include a structure or component for controlling release of the active agent from the composition as it coagulates to form the implant in situ and/or from the formed implant. A controlled release component can be used to facilitate the sustained release of an active agent and control the initial burst of agent from the coagulating composition, and facilitate the safe incorporation of a higher concentration of active agent into an implant. It can also improve the efficiency of the implant because a much greater percentage of an active agent can remain in the implant for sustained release and not be lost during the initial burst effect.

One or more modes of release controlling component can be used. The controlled release component can be, for example, a microstructure ranging in size from about 10 nm to about 500 microns, preferably less than about 150 microns, such as a microcapsule, microparticle such as a liposphere or microsphere, a nanoparticle, liposome, micelle, cage compound such as cyclodextrin, and the like; a macrostructure which size is larger than 500 microns, such as a fiber, film, rod, disc, cylinder, bead, and the like, including a reservoir system containing the active agent within a membrane, or a monolithic system with the active agent distributed throughout a matrix; and/or a low water-solubility salt of the active agent (solubility of 25 mg/l or less, 40° C., 4 hours) that includes, for example, a carboxylate anion as a counterion for the active agent, such as the ionic form of pamoic acid, tannic acid or stearic acid, and the like.

The controlled release component can also be a molecular controlled release system such as a complex or covalently bonded conjugate of the agent associated with a carrier molecule to alter the water solubility and transport properties of the active agent. The carrier molecule can be, for example, a water-insoluble polymer such as polyglycolide, poly(DL-lactide) (PLA), polycaprolactone (PCL), and the like, and copolymers and terpolymers, and combinations and mixture thereof; a water-soluble polymer such as poly(malic acid), polyethylene glycol, poly-L-aspartic acid, poly (glutamic acid), polylysine, dextran and copolymers of N-(2-hydroxypropyl)methacrylamide (HPMA); or a small organic molecule such as stearic acid. A complex in which a carrier molecule is operatively associated with the active agent will break down in water but slow the release of the active agent from the implant. A complex of the active agent and carrier can optionally include a metal cation such as zinc, magnesium, calcium, and the like.

The controlled release component can be dispersed in the composition so that it is embedded within the implant matrix upon solidification in situ. An implant containing a controlled release component provides at least two modes of controlled release of the active agent, one mode based upon the rate of release of the agent from the controlled release component, and another mode based upon the release of the agent from the implant by biodegradation, bioerosion, diffusion and/or leaching from the solid implant. For additional discussion of controlled release components, see U.S. patent application Ser. No. 08/225,140, filed Apr. 8, 1994, the disclosure of which is incorporated by reference herein.

Use of the Non-Polymeric Composition.

The non-polymeric composition can be used for treating a variety of tissue defects of an animal, for example, a tissue with a void such as a periodontal pocket, a wound on the skin, a surgical incision, a bone defect, and the like. Once delivered into or onto in the implant site, the composition will gradually coagulate or precipitate to form a solid, microporous matrix within about 1–5 days, preferably about 1–3 days, preferably within about 2 hours.

For example, the composition can be applied to a defect in bone tissue such as a fracture in an arm or leg bone, a defect in a tooth, and the like. In such application, it is preferable that the bone tissue is surgically separated from the adjacent soft tissue to expose the defect, and the composition then applied to the defect, whereupon the composition hardens in situ to a solid implant.

The solid matrix can also function as a barrier system for guided tissue regeneration by providing a surface over which cells can grow. To enhance regeneration of a hard tissue such as bone tissue, it is preferred that the solid implant matrix provides support for new cell growth that will replace the matrix as it becomes gradually absorbed or eroded by body fluids.

The composition can be delivered onto a tissue, for example, by injection, spraying, squirting, brushing, painting, coating, and the like. Delivery can be via a cannula, catheter, syringe with or without a needle as desired such as a 18–25 gauge needle, pressure applicator, pump, using a brush, and the like. The composition can be applied onto a tissue in the form of a film, for example, to provide a film dressing on the surface of the tissue, and/or to adhere to a tissue to another tissue or implant, among other applications.

For use of the non-polymeric composition to treat periodontal disease, gingival tissue overlying the root of the tooth can be excised to form an envelope or pocket, and the composition delivered into the pocket and against the exposed root where it is allowed to harden to a solid matrix. The composition can also be delivered to a tooth defect by making an incision through the gingival tissue to expose the root, and then applying the material through the incision onto the root surface by brushing, squirting, or other means.

When used to treat a defect on skin or other tissue, an aqueous medium can be applied to the surface of the composition to enhance the coagulation of the non-polymer material.

Advantageously, the coagulating composition is malleable and can be manipulated in the implant site to conform it to the contours of the tissue defect. For example, overlying gingival tissue in a periodontal defect can be urged over the solidifying matrix, and pressure applied to the surface of the tissue to conform the solidifying matrix to the shape and contour of the root and bone. The solid matrix has a firm consistency that ranges from gelatinous to formable and impression-retaining to a rigid structure similar to conventional bone cement.

A solid implant can also be formed from the non-polymeric composition outside the body of the animal and then inserted as a solid matrix into an implant site. For example, the composition may be applied to a support surface such as glass or porcelain that has been coated with water or another aqueous medium, and additional water applied onto the surface of the composition. The solid matrix forms as the solvent dissipates into the adjacent aqueous medium. The implant can then be placed into the implant site of the animal.

The composition can also be applied to an implantable device such as a suture, clasp, prosthesis, catheter, metal screw, bone plate, pin, a bandage such as gauze, and the like, to enhance the compatibility and/or performance or function of an implantable device with a body tissue in an implant site. The non-polymeric system can be coated onto an implantable device, applied to a body tissue and then an implantable device implanted thereon, or the implantable device implanted and coated with the non-polymeric composition. For example, the composition can be applied to the rough surface of an implantable device to enhance the compatibility of the device by providing a smooth surface which reduces the occurrence of abrasions from the contact of rough edges with the adjacent tissue. The non-polymeric system can also be used to enhance the performance or function of an implantable device. For example, the composition can be applied to a gauze bandage to enhance its compatibility or adhesion with the tissue to which it is applied. The composition can be applied around a device such as a catheter or colostomy that is inserted through an incision into the body to secure the catheter/colostomy in place, and/or to fill the void between the device and tissue and form a tight seal to reduce bacterial infection and loss of body fluid. The combination of the non-polymeric composition and an implantable device can also be used to hold tissue in place and/or together, to adhere and/or secure the implantable device to tissue, to fill and/or seal a wound or void, among other uses.

Formulation of the non-polymeric composition and administration of the composition in vivo will ultimately be according to the judgment and protocol of the patient's attending health care professional such as a physician, or if appropriate, a dentist. Choice of the particular formulation of ingredients will be made by the attending health care professional. Without a bioactive agent, the solid implant can function as a structure for promotion of cell growth and tissue repair. With a bioactive agent, the implant will not only function in such capacity but will also deliver the bioactive agent to tissues and/or organs of the animal.

The amounts and concentrations of ingredients in the composition administered to the patient will generally be effective to accomplish the task intended. If that task is to fill a void space, a composition with an effective amount of ingredients will be administered to accomplish this task. For administration of a bioactive agent, the amount and release rate will follow recommendations of the manufacturer of the bioactive agent. Generally, the concentration of a bioactive agent in the composition will be about 0.01–400 mg per gram of the non-polymeric composition.

The invention will be described with reference to various specific and preferred embodiments and techniques. However, it should be understood that many variations and modifications may be made while remaining within the spirit and scope of the invention.

EXAMPLE 1

Cholesterol was mixed with N-methyl-2-pyrrolidone (NMP) and porcine somatotropin-A (PST-A) was added as a powder to obtain a formulation containing 30% by weight cholesterol, 60% by weight NMP, and 10% by weight PST-A. The formulation was then loaded into a 1-cc polypropylene syringe and one drop of formulation was dispelled from the syringe into a tared vial containing phosphate-buffered saline solution at pH 7.4. The weight of the formulation added to the phosphate-buffered saline solution was recorded. The vial was then sealed with a Teflone®-lined screw cap and placed in a 37° C. shaker bath. All samples were run in triplicate. The phosphate-buffered saline solution (PBS) was withdrawn at specified time points and replaced with fresh PBS. The release fluids were stored at 5° C. until analyzed by a Pierce BCA® protein assay. The data showed that the cholesterol implant provided sustained release of the PST-A past 72 hours with cumulative percent releases of 5.3% at 3 hours, 5.4% at 6 hours, 5.5% at 12 hours, 5.8% at 24 hours, and 6.3% at 72 hours.

EXAMPLE 2

Glycerol tristearate (GST) was mixed with N-methyl-2-pyrrolidone (NMP), and porcine somatotropin-A (PST-A) was added to give a formulation with 30% by weight GST, 60% by weight NMP, and 10% by weight PST-A. The release of PST-A from this formulation was determined by the same procedure described above in Example 1. Release of PST-A was sustained out to 7 days with cumulative percent releases of 45.8% after the first day, 53.6% after 2 days, 59.9% after 4 days, and 61.1% after 7 days.

EXAMPLE 3

GST was mixed with dimethyl sulfoxide (DMSO), and PST-A was added to give a formulation with 30% by weight GST, 60% by weight DMSO, and 10% by weight PST-A. Using the sample procedure described in Example 1 above, the release of PST-A from this formulation with DMSO was substantially reduced over that obtained in Example 2 with NMP. The cumulative percent releases were 4.0% after the first day, 5.4% after 2 days, 8.2% after 4 days, and 8.5% after 7 days.

EXAMPLE 4

GST was mixed with DMSO, and sodium carbonate and PST-A were added as powders to give a formulation with 30% by weight GST, 50% by weight DMSO, 10% by weight sodium carbonate, and 10% by weight PST-A. The addition of the water-soluble pore-forming agent, sodium carbonate, substantially increased the release of PST-A from the matrix compared to that without the sodium carbonate described in Example 3 above. Cumulative percent releases were 67.3% after the first day, 69.7% after 3 days, 70.3% after 5 days and 70.8% after 7 days.

EXAMPLE 5

GST was mixed with triethyl citrate (TEC), and PST-A was added as a powder to give a formulation with 30% by weight GST, 60% by weight TEC, and 10% by weight PST-A. The release of PST-A from this formulation was intermediate between that shown with the NMP formulation in Example 2 and the DMSO formulation shown in Example 3. Cumulative percent releases were 15.4% after the first day, 15.9% after 2 days, 16.4% after 4 days, and 16.6% after 7 days.

EXAMPLE 6

Stearic anhydride (SAH) was mixed with NMP, and PST-A was added as a powder to give a formulation with 30% by weight SAH, 60% by weight NMP, and 10% by weight PST-A. Using the same procedure described in Example 1, the release of PST-A was determined from this formulation. Cumulative percent releases were 56.5% after the first day, 58.4% after 2 days, 60.7% after 4 days, and 61.1% after 7 days.

EXAMPLE 7

Glyceryl monolineate (GMOL) obtained from Eastman Chemical Company as Myverol 18-92 was dissolved in DMSO and doxycycline hyclate, a water-soluble antibiotic, was added as a powder to give a formulation containing 59% GMOL, 40% DMSO, and 1% doxycycline hyclate. The formulation was there loaded into a 1-cc polypropylene syringe and one drop of formulation was dispelled from the syringe into a tared vial containing phosphate-buffered saline (PBS) solution at pH 7.4. The weight of the formulation added to the PBS was recorded. The vial was then sealed with a Teflon®-lined screw cap and placed in a 37° C. shaker bath. All samples were run in triplicate. The PBS solution was withdrawn at specified time points and replaced with fresh PBS. The release solutions were then analyzed by ultraviolet spectroscopy (UV) for the concentration of doxycycline hyclate by comparison to standard curves of concentration versus UV absorption. The data showed that the GMOL implant sustained the release of the water-soluble doxycycline hyclate with a cumulative release of 77% after 2 hours and 94% after 5 hours.

EXAMPLE 8

GMOL was dissolved in NMP and doxycycline hyclate was added to give a formulation containing 59% GMOL, 40% NMP, and 1% doxycycline hyclate. The release of doxycycline hyclate from this formulation was determined by the same procedure described in Example 7. This formulation containing NMP gave a faster release than the formulation in Example 7 containing DMSO, with a cumulative release of 90% after 2 hours and 100% after 5 hours.

EXAMPLE 9

GMOL was dissolved in DMSO and doxycycline hyclate was added to give a formulation containing 69% GMOL, 30% DMSO, and 1% doxycycline hyclate. When this formulation containing a higher concentration of GMOL than in Example 7 was evaluated for release of doxycycline, it provided a more sustained release than the formulation in Example 7. The cumulative release of doxycycline was 65% after 2 hours and 79% after 5 hours.

EXAMPLE 10

Glycerol monooleate (GMOO) obtained from Eastman Chemical Company as Myverol 18-99 was dissolved in DMSO and doxycycline hyclate was added as a powder to give a formulation containing 69% GMOO, 30% DMSO, and 1% doxycycline hyclate was added as a powder to give a formulation containing 69% GMO0, 30% DMSO, and 1% doxycycline hyclate. The cumulative release of doxycycline from this formulation was similar to that obtained in Example 9 with the GMOL material with 68% after 2 hours and 79% after 5 hours.

EXAMPLE 11

GMOO was dissolved in NMP and doxycycline hydrate added to give a formulation with 69% GMOO, 30% NMP, and 1% doxycycline hyclate. The release of doxycycline from this formulation was comparable to that obtained in Example 10 with DMSO with cumulative releases of 70% after 2 hours and 84% after 5 hours.

EXAMPLE 12

Acetylated monoglycerides (AMOG) obtained from Eastman Chemicals Company as Myvacet 7-07 was dissolved in NMP and doxycycline hyclate was added to give a formulation containing 69% AMOG, 30% NMP, and 1% doxycycline hyclate. When this formulation was evaluated for drug release as described in Example 7, it was found that this material significantly reduced the rate of release of doxycycline over those formulations described in Examples 8 and 11, with cumulative releases of 2% after 2 hours, 4% after 5 hours, 62% after 8 hours, and 90% after 24 hours.

EXAMPLE 13

The same formulation of GMOL and DMSO described in Example 7 was prepared with naltrexone in place of doxycycline hyclate. The base form of naltrexone, a narcotic antagonist, was used to provide a more hydrophobic drug. However, the cumulative release of naltrexone was similar to that obtained with the more hydrophilic doxycycline hyclate in Example 7 with naltrexone cumulative releases of 77% after 2 hours and 94% after 5 hours.

EXAMPLE 14

The same formulation of GMOL with NMP described in Example 8 was prepared with naltrexone base in place of doxycycline hydrate. The cumulative release of naltrexone was 77% after 2 hours and 100% after 5 hours. This rate was lower than that obtained in Example 8 with the more hydrophilic doxycycline hyclate.

EXAMPLE 15

The same formulation of GMOL with DMSO described in Example 9 was prepared with naltrexone in place of doxycycline hyclate. The cumulative release of naltrexone was 59% after 2 hours and 76% after 5 hours.

EXAMPLE 16

The same formulation of GMOO with DMSO described in Example 10 was prepared with naltrexone in place of doxycycline hyclate. The cumulative release of naltrexone was 59% after 2 hours and 82% after 5 hours.

EXAMPLE 17

The same formulation of GMOO with NMP described in Example 11 was prepared with naltrexone in place of doxycycline hyclate. The cumulative release of naltrexone was 78% after 2 hours and 92% after 5 hours.

EXAMPLE 18

The same formulation of AMOG with NMP described in Example 12 was prepared with naltrexone in place of doxycycline hyclate. This formulation significantly extended the release of naltrexone with cumulative releases of 3% after 2 hours, 11% after 5 hours, 28% after 8 hours, after 24 hours, and 78% after 72 hours.

What is claimed is:

1. A method of treating a tissue defect in an animal, comprising:
    (a) administering a composition to the tissue defect, the composition comprising:
        (i) a non-polymeric, water-insoluble material that is biodegradable; and
        (ii) a biocompatible, organic solvent that at least partially solubilizes the non-polymeric, water-insoluble material and is miscible to dispersible in water or body fluids and capable of dissipating, diffusing or leaching from the composition into body fluid upon placement within a body; and
    (b) allowing the composition to coagulate or precipitate in situ to form a solid implant; wherein the implant is effective to treat the tissue defect.

2. A method of delivering a biologically-active agent to an animal, comprising:
    (a) administering a composition to the animal, the composition comprising:

(i) a non-polymeric, water-insoluble material that is biodegradable;

(ii) a biocompatible, organic solvent that at least partially solubilizes the non-polymeric, water-insoluble material and is miscible to dispersible in water or body fluids and capable of dissipating, diffusing or leaching from the composition into body fluid upon placement within a body; and (iii) the biologically-active agent; and (b) allowing the composition to coagulate or precipitate in situ to form a solid implant; wherein the biologically active agent is delivered to the animal.

3. A method of treating periodontal disease, comprising:

(a) administering to gingival tissue of a patient a composition, the composition comprising:

(i) a non-polymeric, water-insoluble material that is biodegradable; and (ii) a biocompatible, organic solvent that at least partially solubilizes the non-polymeric, water-insoluble material and is miscible to dispersible in water or body fluids and capable of dissipating, diffusing or leaching from the composition into body fluid upon placement within a body; and (b) allowing the composition to coagulate or precipitate in situ to form a solid implant; wherein the implant is effective to treat the periodontal diseased tissue.

4. A method for enhancing the compatibility, function, or both, or a surgically implantable device with a body tissue, comprising:

applying a composition to the surgically implantable device, to a body tissue, or a combination of both, the composition comprising:

(i) a non-polymeric, water-insoluble material that is biodegradable; and (ii) a biocompatible, organic solvent that at least partially solubilizes the non-polymeric, water-insoluble material and is miscible to dispersible in water or body fluids and capable of dissipating, diffusing or leaching from the composition into body fluid upon placement within a body;

wherein the combination of the composition with the device is effective to enhance the compatibility, function, or both, or the implantable device with the body tissue.

5. The method according to claim 1, wherein the non-polymeric material is selected from the group consisting of sterols, cholesteryl esters, $C_{12}$–$C_{24}$ fatty acids, $C_{18}$–$C_{36}$ monoacylglycerides, $C_{18}$–$C_{36}$ diacylglycerides, $C_{18}$–$C_{36}$ triacylglycerides, sucrose fatty acid esters, sorbitan fatty acid esters, $C_{16}$–$C_{18}$ fatty alcohols, esters of fatty alcohols, esters of fatty acids, anhydrides of fatty acids, phospholipids of fatty acids, lysoderivatives of fatty acids, sphingosine, sphingosine derivatives, sphingomyelins, ceramides, glycosphingolipids, lanolin, lanolin alcohols, and mixtures thereof.

6. The method according to claim 5, wherein the non-polymeric material is selected from the group consisting of stearyl sphingomyelin, palmitoyl sphingomyelin, tricosanyl sphingomyelin, stearyl ceramide, palmitoyl ceramide, and mixtures thereof.

7. The method according to claim 5, wherein the non-polymeric material is selected from the group consisting of cholesterol, glyceryl monostearate, glyceryl tristcarate, stearic acid, stearic anhydride, glyceryl monooleate, glyceryl monlinoleate, and mixtures thereof.

8. The method according to claim 1, wherein the solvent is selected from the group consisting of N-methyl-2-pyrrolidone, 2-pyrrolidone, propylene carbonate, dimethyl carbonate, ethanol, acetic acid, ethyl acetate, ethyl lactate, methyl acetate, acetone, methyl ethyl ketone, isopropylidene glycol, glycerol formal, glycofurol, dimethylformamide, dimethyl sulfoxide, dimethylsulfone, tetrahydrofuran, caprolactam, N,N-dimethyl-m-toluamide, 1-dodecylazacycloheptan-2-one, and mixtures thereof.

9. The method according to claim 1, wherein the solvent is selected from the group consisting of N-methyl-2-pyrrolidone, 2-pyrrolidone, dimethylsulfoxide, ethyl lactate, propylene carbonate, glycofurol, glycerol formal, isopropylidene glycol, and mixtures thereof.

10. The method according to claim 1, wherein the solvent comprises a mixture of a first solvent capable of dissolving the non-polymeric material, and a second solvent incapable or less capable than the first solvent of dissolving the non-polymeric material; the first and second solvents included in said mixture at a ratio to at least partially dissolve the non-polymeric material therein; wherein upon placement of the composition within the body, the first solvent dissipates, disperses, or leaches into body fluid thereby resulting in an increase in the ratio of the second solvent to the first solvent whereupon the non-polymeric material precipitates or coagulates to form the solid matrix.

11. The method according to claim 10, wherein the first solvent is selected from the group consisting of N-methyl-2-pyrrolidone, 2-pyrrolidone, acetone, ethyl acetate, methyl acetate, methyl ethyl ketone, dimethylformamide, dimethyl sulfoxide, glycerol formal, glycofurol, isopropylidene glycol, tetrahydrofuran, caprolactam, and mixtures thereof.

12. The method according to claim 10, wherein the second solvent is selected from the group consisting of water, ethanol, propylene glycol, and polyethylene glycol.

13. The method according to claim 1, wherein the biologically active agent is selected from the group consisting of an antibacterial agent, antimicrobial agent, antifungal agent, antiviral agent, and mixtures thereof.

14. The method according to claim 1, wherein the biologically-active agent is selected from the group consisting of an anti-inflammatory agent, antiparasitic agent, analgesic agent, anesthetic agent, immunogen, growth factor, anti-neoplastic agent, hormone, antihistamine, osteoinductive agent, cardiovascular agent, anti-ulcer agent, bronchodilating agent, vasodilating agent, central nervous system agent, antipsychotic agent, and mixtures thereof.

15. The method according to claim 1, wherein the biologically-active agent is a growth factor selected from the group consisting of platelet-derived growth factor, insulin-derived growth factor, transforming growth factor-$\alpha$, transforming growth factor-$\beta$, epidermal growth factor, fibroblast growth factor, interleukin-1, and mixtures thereof.

16. The method according to claim 1, wherein the biologically-active agent is tetracycline or doxycycline.

17. The method according to claim 1, wherein the composition further comprises a controlled release component that comprises the active agent.

18. The method according to claim 1, wherein the composition further comprises a pore-forming agent selected from the group consisting of a sugar, a salt, a water-soluble polymer, and a water-insoluble substance that rapidly degrades to a water-soluble substance.

19. The method according to claim 1, wherein the composition further comprises a release rate modification agent for controlling the rate of release of a biologically active agent in vivo from the implant matrix.

20. The method according to claim 19, wherein the release-rate modification agent is an organic solvent different from the organic solvent of claim 1(b), selected from the group consisting of dimethyl adipate, propylene glycol, polyethylene glycol, ethyl heptanoate, glycerol triacetate, dimethyl phthalate, and mixtures thereof.

* * * * *